United States Patent [19]
Greening et al.

[11] Patent Number: 5,701,912
[45] Date of Patent: Dec. 30, 1997

[54] STEREOPHONIC SYSTEM FOR MINIMALLY INVASIVE SURGERY

[75] Inventors: Anthony B. Greening, North Vancouver; Thomas N. Mitchell, Richmond, both of Canada

[73] Assignee: International Telepresence Corporation, Vancouver, Canada

[21] Appl. No.: 576,719

[22] Filed: Dec. 21, 1995

[51] Int. Cl.$^6$ .................. A61B 1/02; A61B 7/04
[52] U.S. Cl. ............... 128/773; 128/715; 381/67
[58] Field of Search .................... 128/897, 715, 128/773; 381/67; 604/116, 117

[56] References Cited

U.S. PATENT DOCUMENTS

| | | | |
|---|---|---|---|
| 4,248,241 | 2/1981 | Tacchi | 128/671 |
| 4,299,230 | 11/1981 | Kubota | 128/630 |
| 4,304,240 | 12/1981 | Perlin | 128/715 |
| 4,577,638 | 3/1986 | Graham | 128/773 |
| 4,672,977 | 6/1987 | Kroll | 128/715 |
| 4,967,760 | 11/1990 | Bennett, Jr. et al. | 128/715 |
| 4,981,139 | 1/1991 | Pfohl | 128/671 |
| 5,076,284 | 12/1991 | Joyce et al. | 128/773 |
| 5,191,892 | 3/1993 | Blikken | 128/715 |
| 5,389,077 | 2/1995 | Melinyshyn et al. | 604/117 |
| 5,467,775 | 11/1995 | Callahan et al. | 128/773 |
| 5,492,129 | 2/1996 | Greenberger | 128/715 |
| 5,539,831 | 7/1996 | Harley | 381/67 |

*Primary Examiner*—Marvin M. Lateef
*Assistant Examiner*—Carl H. Layno
*Attorney, Agent, or Firm*—Townsend and Townsend and Crew LLP

[57] ABSTRACT

A stereophonic system is included in an instrument for minimally invasive surgery which permits a surgeon to hear spatial sounds from within a body wall. The instrument comprises a cylindrical member with an internal end for positioning inside the body wall and an external end to remain outside the body wall. There are two audio channels provided on opposing sides of the cylindrical member extending longitudinally from acoustic openings at the internal end to the external end, acoustical diaphragms protect the openings at the internal end, and a microphone is connected to each of the two audio channels at the exterior end of the cylindrical member, each microphone producing an audio signal from each of the two audio channels. A stereophonic audio amplifier amplifies the signal from each microphone and a stereophonic acoustical system produces stereophonic sound.

9 Claims, 2 Drawing Sheets

STEREOPHONIC SYSTEM FOR MINIMALLY INVASIVE SURGERY

TECHNICAL FIELD

The present invention relates to minimally invasive surgery and more specifically to an instrument for providing stereophonic sound from inside a living body wall for assisting in the performance of minimally invasive surgery.

BACKGROUND ART

Minimally invasive surgical techniques are today replacing many conventional surgical procedures as they reduce the trauma of entering body cavities within a living body wall. Body cavity penetrating instruments for minimally invasive surgery include insufflation needles and trocar/cannular sleeve assemblies.

An example of placing a trocar/cannular sleeve in a body wall is to initially insert an insufflation needle through a small incision in the body wall through to the cavity where the operation is to occur. An insufflating gas such as carbon dioxide is passed through the needle to pressurize the cavity, the needle is then removed and a trocar/cannular sleeve assembly is inserted. This assembly includes a sleeve into which is inserted a trocar having a three bladed knife at the end thereof. The knife punctures the body wall and enters the body cavity. The trocar is then removed leaving the trocar/cannular sleeve, hereinafter referred to as a "trocar sleeve", inserted through the body wall into the cavity. A seal at the external end of the trocar sleeve prevents gas escaping from the body cavity, and a gas connection on the trocar sleeve permits insufflating gas to enter the body cavity and maintains the pressure therein. An endoscopic camera or the like may be inserted into the body cavity through the trocar sleeve. Thus, a surgeon is able to view the body cavity. Additional incisions are then made at strategic locations and additional trocar sleeve assemblies are introduced to provide access for surgical instruments necessary to perform the operation inside the body cavity.

In existing minimally invasive surgery, an endoscope with a video screen is used to provide a picture for a surgeon who is able to see inside the body cavity and direct the surgical instruments through other trocar sleeves. Whereas this picture provides some information to a surgeon, it does not provide spatial sound and it is known that most information received by a human brain relating to the position of a body in space comes from the eyes, some of this information comes from the ears in the form of sound and particularly spatial sound which positions the location of a sound in space. The ears of most mammals, including humans, are able to locate the position of sound relative to the position of the ears.

It has been shown that in order to provide spatial sound through an audio system it is necessary to produce a head shaped configuration with microphones representing ears so that it simulates the position of ears on a head. When this is achieved a person listening to the stereophonic sound from these microphones receives spatial sound providing not only left and right location of sound but also vertical location. One headphone manufacturer produces a microphone for spatial audio recordings in studio applications.

The reason for requiring audible sound from inside a body cavity is to detect, first of all, the noise that may occur from inserting other trocar sleeves into the body cavity locating sounds from these other instruments as they are being inserted through the body wall to ensure they are located at appropriate positions for surgery. Also, it enables surgeons to hear if there is blood coming from minor incisions or the like that have occurred due to instrument tips nicking or puncturing vessels, organs, or other structures in the body cavity. By having the stereophonic spatial information, one is able to identify where the sound is coming from within the body cavity without having to rely on only an endoscope which allows one to see into the cavity. The stereoscopic spatial information also positions sounds from the clash or collision of two or more endoscopic instruments. The stereophonic spatial information allows a surgeon to know whether the sound emanates outside of the picture seen by the endoscopic camera. A variation in the flow of blood coming from different blood vessels and other tissues has different sounds and a surgeon can determine the quantity of blood flowing from these nicks and incisions either in the cavity or in the body wall.

SUMMARY OF THE INVENTION

It is an aim of the present invention to provide an instrument that enters a living body wall for assisting in the performance of minimally invasive surgery and has a stereophonic system to hear sound emanating from within the body wall and provide spatial location of the sound.

The present invention provides an instrument for entering a living body wall for assisting in the performance of minimally invasive surgery, comprising a cylindrical member with an internal end for positioning inside the body wall and an external end to remain outside the body wall, two audio channels on opposing sides of the cylindrical member extending longitudinally from acoustic openings at the internal end to the external end of the cylindrical member, acoustical diaphragms over the openings at the internal end of the cylindrical member, a microphone connected to each of the two audio channels at the exterior end of the cylindrical member, each microphone producing an audio signal from each of the two audio channels, a stereophonic audio amplifier for amplifying the signal from each microphone, and a stereophonic acoustical system to produce stereophonic sound.

BRIEF DESCRIPTION OF DRAWINGS

In drawings which illustrate embodiments of the present invention.

DESCRIPTION OF THE PREFERRED EMBODIMENT

Figure 1:
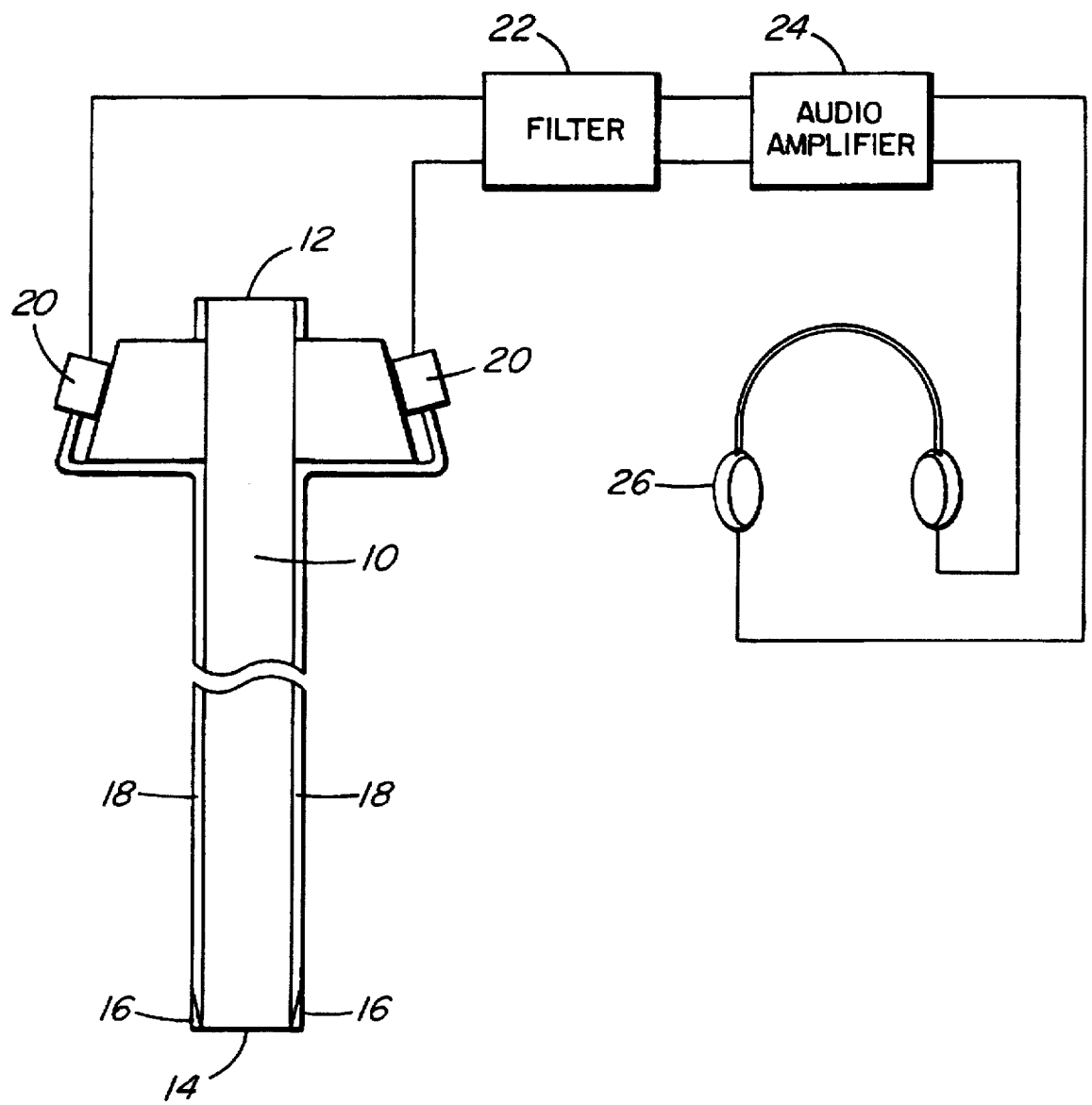
FIG. 1 is a schematic view showing a trocar sleeve equipped with a stereophonic system according to one embodiment of the present invention.

FIG. 1 illustrates a trocar sleeve 10 having an access aperture for the distal end of the trocar tool (not shown) to be inserted therethrough. Also, the trocar sleeve 10 may be used in association with an endoscope, other type of scope or a surgical instrument that passes into the body cavity through the tube 10. While not shown, an attachment for gas and a seal may be supplied on the external end 12 of the tube 10 so that an insufflating gas such as carbon dioxide may retain pressure within the body cavity. At the internal end 14 or distal end of the sleeve 10 are two acoustic openings 16 leading to two separate audio channels 18 which extend up and are connected to two microphones 20 adjacent the external end 12 of the sleeve 10. Signals from the microphones 20 are shown passing through a filter 22 which is used to filter out sounds such as carbon dioxide gas flow used to inflate the cavity or, alternatively, to accentuate specific sounds such as heart or blood flow. The filter 22 is not essential and in some instances there is no need to filter the signals which pass through an audio amplifier 24 connected to a stereophonic acoustic system in the form of a pair of stereophonic binaural headphones 26.

Figure 2:
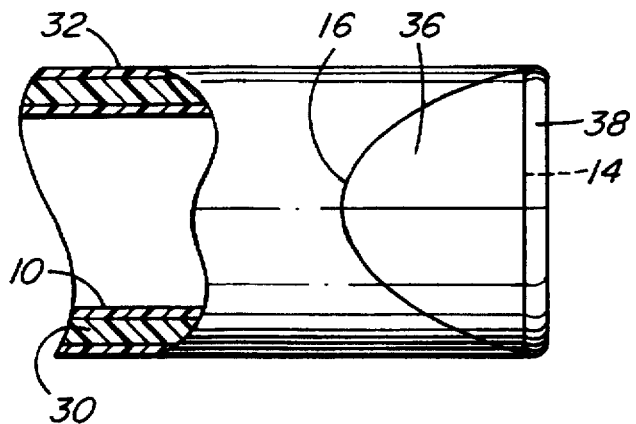
FIG. 2 is a partial side view showing an internal end of a trocar sleeve with an acoustic opening to an audio channel.
Figure 3:
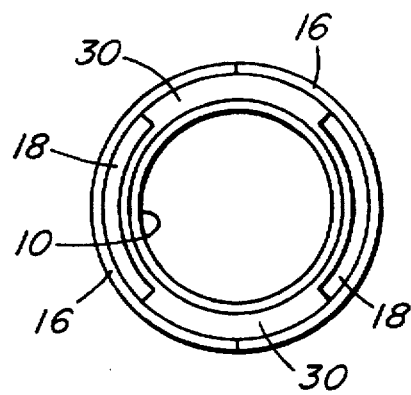
FIG. 3 is an end view showing the internal end of the trocar sleeve of FIG. 2.
Figure 4:
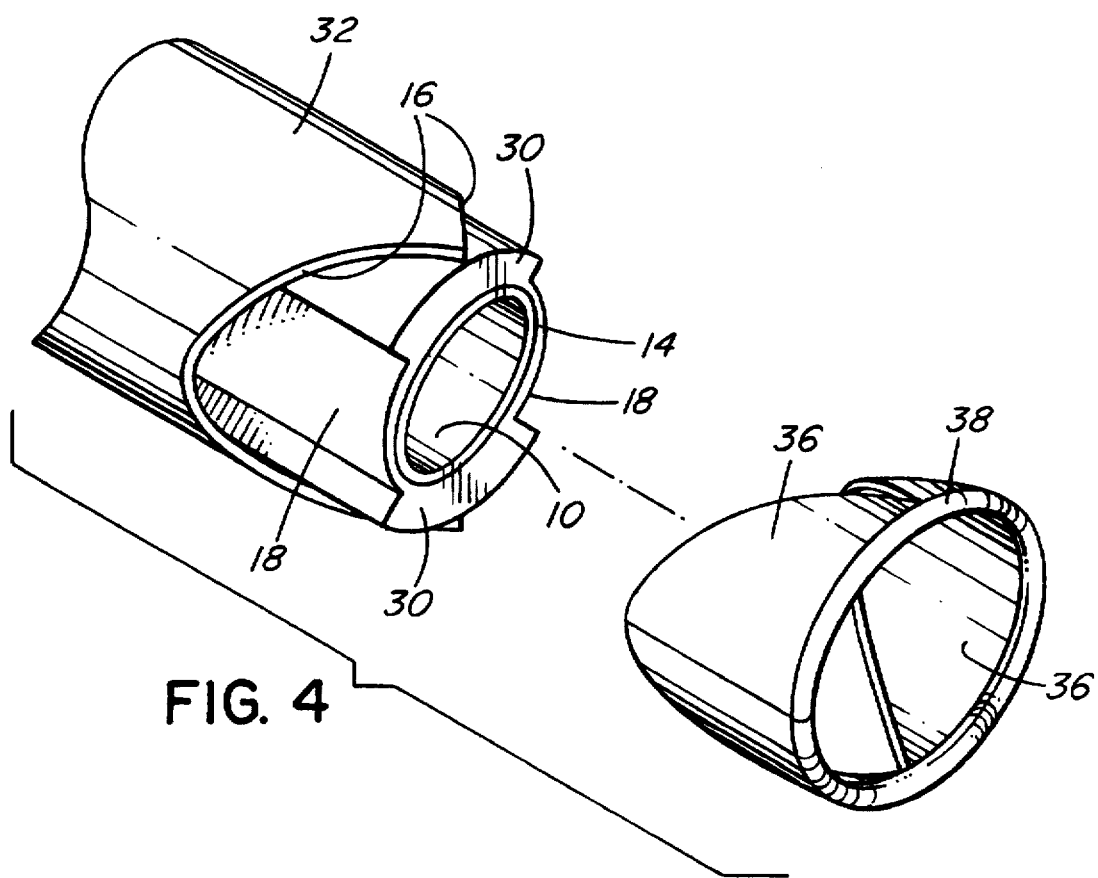
FIG. 4 is an exploded isometric view showing the end of the trocar sleeve of FIG. 2 with an acoustic diaphragm support ring shown separately.

FIGS. 2 to 4 illustrate details of the trocar sleeve 10. The sleeves 10 may be made of plastic in which case they are generally disposable or, alternatively, are made of stainless steel and may be sterilized and reused. Left and right audio channels 18 are formed by opposing circular ring sector shaped cutouts in a sleeve 30 made of material that provides an acoustical barrier to prevent sound passing therethrough. The sleeve 30 fits over the trocar sleeve 10 and provides a mechanical support for an external layer 32 made of a material which provides an acoustical barrier for the audio channels 18 in the sleeve 30.

The opening 16 for each of the audio channels 18 is cup shaped and is formed by cutting back the external layer 32 thereby exposing the audio channel 18. The shape of the openings 16 is arranged to provide spatial hearing simulate a pair of ears in a head of a mammal. It is known that most mammals have spatial hearing which provide not only left and right audio information, but also vertical audio information. Thus, by simulating ears on a mammalian head, the use of the stereophonic headphones in effect places a person inside the body cavity at the location of the acoustic openings 16 and hears the sound spatially in the cavity.

The righthand audio channel 18 is linked up to a microphone 20 that leads to a right phone or ear piece and the lefthand audio channel 18 is linked to a microphone 20 that is linked to a left phone or ear piece of a set of stereophonic headphones 26. Thus, the trocar sleeve 10 is rotated to an aligned position representing the alignment of a person's head. For example, if a surgeon was operating from one side of the body, then the trocar sleeve 10 would be positioned so the acoustic openings 16 were aligned left and right to the left and right phones of the ear phones 26. If he were to move to the other side of the body, the trocar sleeve 10 may be rotated so the openings 16 are aligned with the ear phones 26.

An acoustic diaphragm in the form of a membrane 36 covers each of the openings 18 at the internal end 14 of the sleeve 10. The membrane 36 is liquid and debris impervious to prevent liquid or debris entering the audio channels 18 but does not muffle sound. The membrane 36 has to be able stand up to gas pressure to prevent the escape of gas the from the body cavity. The membranes 36 are provided for both openings 16 and have an acoustic diaphragm support ring 38 as shown in FIG. 4 to locate the membranes or acoustic diaphragms 36 and retain them in position over the internal end 14 of the trocar sleeve 10. The acoustic diaphragm support ring does not interfere with insertion of the trocar sleeve 10 through the body wall, or the passage of scopes and instruments through the sleeve 10.

Whereas the instrument is shown as being a trocar sleeve 10, the stereophonic system can be applied to, for example, an endoscope having a cylindrical shape at an internal tip, the audio openings 16 are positioned on each side of the internal tip of the endoscope or other instrument so that the stereophonic system works together with the viewing system from the endoscope. This simulates having eyes and ears inside a body cavity. In a still further embodiment the endoscope may provide three dimensional viewing, thus combining three dimensional viewing with the stereophonic system of the present invention a surgeon is able to see with both eyes and both ears inside the body wall.

Whereas the audio channels 18 are shown and illustrated as each having a circular ring sector cross-section, it will be apparent that the audio channels 18 may be in small circular tubes extending up on both sides of a trocar sleeve 10 provided the audio channels transfer sound from the acoustic openings 16 at the internal end 14 of the instrument to the microphones 20. The orientation of the instrument is important to ensure that the righthand and lefthand acoustic openings 16 align with the right ear phone and left ear phone of the stereo binaural headphones 26.

Various changes may be made to the embodiments shown herein without departing from the scope of the present invention which is limited only by the following claims.

We claim:

1. An instrument for entering a living body wall for assisting in the performance of minimally invasive surgery, comprising:

a cylindrical member with an internal end for positioning inside the body wall and an external end to remain outside the body wall;

two audio channels on opposing sides of the cylindrical member extending longitudinally from acoustic openings at the internal end to the external end of the cylindrical member;

acoustical diaphragms over the openings at the internal end of the cylindrical member;

a microphone connected to each of the two audio channels at the external end of the cylindrical member, each microphone producing an audio signal from each of the two audio channels;

a stereophonic audio amplifier connected to each microphone of the two audio channels, the amplifier for amplifying the signal from each microphone, and a stereophonic acoustical system to produce stereophonic sound.

2. The instrument according to claim 1 wherein the acoustical diaphragm comprises a liquid and debris impervious material which does not muffle sound.

3. The instrument according to claim 1 including a filter to accentuate specific sounds and filter extraneous sounds.

4. The instrument according to claim 1 wherein the stereophonic acoustic system comprises stereophonic binaural headphones and wherein the acoustic openings are a lefthand opening and righthand opening, the lefthand opening connected to a left phone of the headphones and the righthand opening connected to a right phone of the headphones.

5. The instrument according to claim 1 wherein the acoustic openings have a contoured shape designed for stereo spatial sound.

6. The instrument according to claim 5 wherein the contoured shape of the acoustic openings simulate ears on a mammalian head.

7. The instrument according to claim 1 wherein the cylindrical member comprises a surgical trocar sleeve with a centre aperture for access through the body wall for insertion of an endoscope, or other type of scope or surgical instrument.

8. The instrument according to claim 7 wherein the audio channels are positioned within an external layer around the trocar sleeve and each of the audio channels have a circular ring sector cross-section with acoustic barriers therebetween.

9. The instrument according to claim 8 wherein the acoustic openings have a tapered shape around the internal end of the cylindrical member.

* * * * *